United States Patent
Majeed et al.

(10) Patent No.: US 10,548,902 B1
(45) Date of Patent: Feb. 4, 2020

(54) TELOMERASE ENHANCEMENT POTENTIAL OF ECDYSTERONE

(71) Applicants: Muhammed Majeed, Edison, NJ (US); Kalyanam Nagabhushanam, East Windsor, NJ (US); Lakshmi Mundkur, Bangalore (IN)

(72) Inventors: Muhammed Majeed, Edison, NJ (US); Kalyanam Nagabhushanam, East Windsor, NJ (US); Lakshmi Mundkur, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/227,033

(22) Filed: Dec. 20, 2018

(51) Int. Cl.
| | | |
|---|---|---|
| *A61K 31/56* | (2006.01) |
| *A61K 31/568* | (2006.01) |
| *A61Q 7/00* | (2006.01) |
| *A61P 17/18* | (2006.01) |
| *A61Q 19/08* | (2006.01) |
| *A61P 17/14* | (2006.01) |
| *A61K 8/63* | (2006.01) |

(52) U.S. Cl.
CPC .............. *A61K 31/568* (2013.01); *A61K 8/63* (2013.01); *A61K 31/56* (2013.01); *A61P 17/14* (2018.01); *A61P 17/18* (2018.01); *A61Q 7/00* (2013.01); *A61Q 19/08* (2013.01)

(58) Field of Classification Search
CPC ...................................................... A61K 31/56
See application file for complete search history.

(56) References Cited

PUBLICATIONS

Priya et al. International Journal of Bioassays, 2015, vol. 4, No. 10, pp. 4401-4404.*

* cited by examiner

*Primary Examiner* — Samira J Jean-Louis

(57) ABSTRACT

Disclosed is a method for enhancing the activity of telomerase using a composition containing ecdysterone. The invention also discloses the use of a composition containing ecdysterone and/or an extract containing ecdysterone, isolated from a plant source in preventing/delaying cell aging in mammals by increasing the activity of telomerase.

2 Claims, No Drawings

TELOMERASE ENHANCEMENT POTENTIAL OF ECDYSTERONE

BACKGROUND OF THE INVENTION

Field of the Invention

The invention in general relates to ecdysterone compositions. More specifically the present invention relates to telomerase enhancing potential of ecdysterone and related biological effects.

Description of Prior Art

Telomeres are very specialized DNA sequences, present in the end of linear chromosomes that help in maintaining the integrity of chromosomes. It is a well known fact that the length of these telomeres shortens with every cell division and plays a pivotal role in cell aging. A ribonucleoprotein DNA polymerase complex—Telomerase, helps to maintain the length of the telomeres. Without the activity of telomerase, the length of telomeres progressively shortens, thereby limiting cell growth (Peter J. Hornsby, Telomerase and the aging process, Exp Gerontol. 2007 July; 42(7): 575-581). Telomere shortening plays a major role in the development of many diseases. In a landmark study, Ornish et. al reported that adopting a healthy lifestyle increased the telomerase activity in peripheral blood mononuclear cells (PBMC). The study noted that healthy diet, exercise, and stress management led to reductions in psychological distress and low-density lipoprotein cholesterol, resulting in a significant (30%) increase in telomerase activity (Ornish D, Lin J, Daubenmier J, et al. Increased telomerase activity and comprehensive lifestyle changes: a pilot study. Lancet Oncol 2008; 9: 1048-57.) The following prior art documents disclose the potential and role of telomeres and telomerase in human health and disease:

1. Peter J. Hornsby, Telomerase and the aging process, Exp Gerontol. 2007 July; 42(7): 575-581
2. Zvereva et al., Telomerase: structure, functions, and activity regulation, Biochemistry (Mose). 2010 December; 75(13):1563-83.
3. Mary Armanios, Syndromes of Telomere Shortening, Annu Rev Genomics Hum Genet. 2009; 10: 45.
4. Masood A. Shammas, Telomeres, lifestyle, cancer, and aging, Curr Opin Clin Nutr Metab Care. 2011 January; 14(1): 28-34.
5. Caldo and Young, Telomere Diseases, N Engl J Med. 2009 Dec. 10; 361(24): 2353-2365.
6. Telomeres and telomerase, https://www.khanacademy.org/science/biology/dna-as-the-crenetic-material/dna-replication/a/telomeres-telomerase (accessed on 24 Sep. 2018)

Evidence suggests that increasing the activity of telomerase, through intervention, helps in increasing the length of telomeres and thereby delaying cell aging. Identifying natural plant-based molecules that are safe, non-toxic and cheap is warranted to efficiently increase the activity of telomeres and delay cell aging.

Ecdysteroids are well studied as plant and insect growth factors. They derive their name from the process of molting in insects, called ecdysis. The common ecdysteroids include ecdysone, ecdysterone and turkesterone, which share the same general properties, but varying in potency and biological effects (https://examine.com/supplements/ecdysteroids/Accessed on 22 Aug. 2018). The following prior art documents list the biological effects of ecdysteroids, particularly ecdysterone:

1. Catalan et al., Ecdysterone induces acetylcholinesterase in mammalian brain, Biochem Physiol C. 1984; 78(1): 193-5.
2. Chaudhary et al., Effect of ecdysone on glutamic decarboxylase in rat brain, Experientia, 1969, 25(3):250-251.
3. Gorelick-Feldman et al., Ecdysteroids elicit a rapid Ca2+ flux leading to Akt activation and increased protein synthesis in skeletal muscle cells, Steroids. 2010; 75(10): 632-7.
4. Parr et al., Estrogen receptor beta is involved in skeletal muscle hypertrophy induced by the phytoecdysteroid ecdysterone, Mol Nutr Food Res. 2014; 58(9):1861-72.
5. Simon et al., Steroid control of longevity in *Drosophila melanogaster*, Science. 2003; 299(5611):1407-10.
6. Kizelsztein et al., 20-Hydroxyecdysone decreases weight and hyperglycemia in a diet-induced obesity mice model, Am J Physiol Endocrinol Metab. 2009; 296(3): E433-E439. Ishimoto and Kitamoto, The Steroid Molting Hormone Ecdysone Regulates Sleep in Adult *Drosophila melanogaster*, Genetics. 2010; 185(1): 269-281.

Ecdysteroids are present in 5-6% of plant species, which include, but not limited to *Achyranthes aspera, Gomphrena celosioides, Trianthema portulacastrum, Sida rhombifolia, Tinospora cordifolia* and *Sesuvium portulacastrum, Ajuga iva, Spinacia oleracea Chenopodium quinoa* (Banerji et al., Isolation of ecdysterone from Indian plants, Phytochemistry, Volume 10, Issue 9, September 1971, Pages 2225-2226, Dinan L, Distribution and levels of phytoecdysteroids within individual plants of species of the Chenopodiaceae. Eur J Entomol 92:295-300 (1995). Marco M P, Sanchez-Baeza F J, Camps F and Coll J, Phytoecdys-'teroid analysis by high-performance liquid chromatography—thermospray mass spectrometry. J Chromatogr A 641:81-87 (1993)). The present invention discloses a novel application of ecdysterone in increasing telomerase activity and its related biological applications.

The principle objective of the invention is to disclose a method of enhancing the activity of telomerase using a composition containing ecdysterone.

It is another objective of the invention to disclose the use of a composition containing ecdysterone in preventing/delaying cell aging.

It is another objective of the invention to disclose the induction of hair growth by increasing the activity of telomerase.

The invention solves the above mentioned objectives and provides further related advantages.

SUMMARY OF THE INVENTION

The present invention pertains to compositions containing ecdysterone. The invention discloses a method of enhancing the activity of telomerase using a composition containing ecdysterone. The invention also discloses the use of a composition containing ecdysterone or an extract containing ecdysterone, isolated from a plant source in preventing/delaying cell aging.

Other features and advantages of the present invention will become apparent from the following more detailed description, which illustrate, by way of example, the principle of the invention.

DESCRIPTION OF THE MOST PREFERRED EMBODIMENTS

In the most preferred embodiment, present invention relates to a method of enhancing the telomerase activity in mammalian cells, said method comprising step of bringing into contact mammalian cells with an effective concentration of ecdysterone, to bring about the effect of telomerase enhancement. In a related embodiment, the mammalian cells are preferably human cells.

In another preferred embodiment, the invention discloses a method of preventing and/or delaying cell aging in mammals by enhancing the activity of telomerase, said method comprising steps of administering a composition containing ecdysterone, isolated from a plant source, to mammals, to bring about prevention and/or delay in cell aging. In a related embodiment, prevention and/or delay in cell aging is brought about by the increase in telomere length resulting from enhancement of telomerase activity. In yet another related embodiment the composition is formulated with pharmaceutically/nutraceutically acceptable excipients, adjuvants, bases, diluents, carriers, conditioning agents, bioavailability enhancers, antioxidants and preservatives and administered orally in form of tablets, capsules, syrups, gummies, powders, suspensions, emulsions, chewables, candies and eatables. In yet another related embodiment the composition is formulated with pharmaceutically/cosmeceutically acceptable excipients, adjuvants, bases, diluents, carriers, conditioning agents, bioavailability enhancers, antioxidants and preservatives and/or incorporated into formulations containing skin care ingredients and administered orally in the form of creams, gels, lotions, powder, serum, oil, suspensions and ointments. In a related embodiment, the mammal is preferably human.

In yet another preferred embodiment, the invention discloses a method for inducing hair growth in mammals, said method comprising step of administering a composition containing ecdysterone to mammals to bring about an increase in hair growth. In a related embodiment, induction of hair growth is brought about by the enhancement of telomerase activity. In a related embodiment, the composition is formulated with pharmaceutically/cosmeceutically acceptable excipients, adjuvants, bases, diluents, carriers, conditioning agents and preservatives and/or incorporated into formulations containing hair care ingredients and administered topically in the form of creams, gels, lotions, shampoo, serum, oil, suspensions, emulsions, and compacts.

The specific examples included herein below illustrate the aforesaid most preferred embodiments of the present invention.

EXAMPLES

Example 1: Telomerase Activity

Methodology

The assay was carried out using Telo TAGGG telomerase PCR ELISA kit (Roche). It allows highly specific amplification of telomerase mediated elongation products followed by detection through ELISA. In the first step telomerase adds the telomeric repeats (TTAGGG) tot eh 3' end of the biotin labeled synthetic P1 primer. In the second step these elongation products are amplified using P2 and P1 primers generating telomerase specific 6 bp increments. PCR product is denatured and hybridized to a digioxigenin labeled telomere repeat specific detection probe. The resultant product is bound to a streptavidin specific miroplate via biotin labeled primer 1. The bound products are detected using anti digioxigenein antibody conjugated to horse radish peroxidase. The enzyme reaction is visualized using TIVIB substrate.

$2 \times 10^5$ PBMCs isolated from blood were seeded in RPMI 1640 medium in 6 well plates. Cells were treated with 10 μg/ml PHA along with different concentrations of ecdysterone/extracts containing ecdysterone. Cells were incubated in a humidified atmosphere with 5% $CO_2$ for 48 hours. After 48 hours of incubation, cells were harvested and centrifuged at 3000 g for 10 minutes at 4° C. Supernatant was removed and PBS was added and centrifuged again. Pellet was suspended in lysis reagent on ice (TeloTAGGG™ Telomerase PCR ELISA). Suspension was retero pipetted at least thrice and incubated for 20 minutes on ice and centrifuged at 16000 g for 20 minutes at 4° C. TRAP assay followed by ELISA was performed as per manufacturer's instructions (TeloTAGGG™ Telomerase PCR ELISA, Merck).

Results

Table 1 shows the telomerase enhancement potential of purified ecdysterone.

TABLE 1

| Telomerase enhancement activity of Ecdysterone | |
|---|---|
| Ecdysterone Assay % | % increase in Telomerase activity |
| 0.5 μg/ml | Nil |
| 0.25 μg/ml | 63.31% |
| 0.125 μg/ml | 64.7 |
| 0.062 μg/ml | 62.1 |

Purified ecdysterone showed significant increase in telomerase activity at concentrations of 0.062-0.25 μg/ml Ecdysterone from Plant Sources:

The ecdysterone content and the telomerase enhancement potential of ecdysterone isolated for plant sources were evaluated. Table 2 provides the telomerase enhancement potential of ecdysterone isolated from *Sida rhombifolia* and *Tinospora cordifolia*.

TABLE 2

| Ecdysterone content and Telomerase activity from plant sources | | |
|---|---|---|
| Batch Number | Ecdysterone Assay % | % increase in Telomerase activity at 12.5 μg/ml |
| Sida rhombifolia | 2.80% | 76.8% |
| Sida rhombifolia | 1.56% | 64.6% |
| Sida rhombifolia | 0.89% | 46.2% |
| Tinospora cordifolia | 1% | 54.65% |

The results indicated that *Sida rhombifolia* and *Tinospora cordifolia* have good ecdysterone content and exhibited excellent telomerase enhancement potential.

The enhancement of telomerase has an important biological significance. It would play a very important role in mitigating diseases like bone marrow failure, dyskeratosis congenital, acquired aplastic anemia, pulmonary fibrosis, liver diseases, chromosomal instability, inflammation, cancers, heart diseases, aging and neurodegenerative diseases, (Caldo and Young, Telomere Diseases, N Engl J Med. 2009 Dec. 10; 361(24): 2353-2365). Since telomerase also plays an important role in skin aging (Boukamp P, Skin aging: a role for telomerase and telomere dynamics? Curr Mol Med. 2005 March; 5(2):171-7), compositions/plant extracts containing ecdysterone find important application in the development of skin care products.

Mammalian hair follicle, harbors multipotent stem cells and that cycles between state of active growth and resting phase. A small number of stem cells in the base of the follicle get activated during the period of hair synthesis. Activation of telomerase can induce anagen phase and increase hair growth (Sarin K Y, Cheung P, Gilison D, et al. Conditional telomerase induction causes proliferation of hair follicle stem cells. Nature. 2005; 436(7053):1048-52.

Example 2: Formulations Containing Ecdysterone for General Health

The compositions containing ecdysterone can be formulated with pharmaceutically/nutraceutically acceptable excipients, adjuvants, bases, diluents, carriers, conditioning agents, bioavailability enhancers, antioxidants and preservatives and administered orally in form of tablets, capsules, syrups, gummies, powders, suspensions, emulsions, chewables, candies and eatables and administered for general health and well being.

In a related aspect, one or more bioavailability enhancers are selected from the group, but not limited to, piperine, tetrahydropiperine, quercetin, Garlic extract, ginger extract, and naringin.

In another related aspect, one or more anti-oxidants and anti-inflammatory agents are selected from the group consisting of, but not limited to, vitamin A, D, E, K, C, B complex, rosmarinic acid, Alpha Lipoic Acid, oxyresveratrol, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosyl-rutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

The following illustrative examples lists some compositions containing ecdysterone:

TABLE 3

| Ecdysterone Tablet |
| --- |
| Active Ingredients |
| Extract containing ecdysterone |
| Excipients |
| Microcrystalline cellulose, Colloidal silicon dioxide, Magnesium stearate |

TABLE 4

| Ecdysterone Capsule |
| --- |
| Active Ingredients |
| Extract containing ecdysterone |
| Excipients |
| Microcrystalline cellulose |

In a related aspect, one or more skin care ingredients are selected from the group consisting of, but not limited to, Alpha Lipoic Acid, oxyresveratrol, Beet root extract, *Boswellia serrata* Extract, β boswellic acids, *Boswellia serrata* oil, *Centella asiatica* Extract, triterpenes, *Garcinia indica* extract, anthocyanins, *Cocos nucifera* extract and juice, *Coleus forskohlii* Extract, forskolin, *Coleus forskohlii* Oil, Tetrahydropiperine, Ellagic Acid, Gallnut Extract, polyphenols, Galanga Extract, Glycyrrhizinic Acid, Green Tea Extract, Epigallocatechin Gallate, Licorice extract, Mono-Ammonium Glycyrrhizinate, Limonoids, Oleanolic Acid, Cosmetic peptides (Oleanolic acid linked to Lys-Thr-Thr-Lys-Ser, Oleanolic acid linked to Lys-Val-Lys), Oleuropein, Piper longumine extract, piperine, Ellagic acid, Pomegranate Extract (Water Soluble), pterostilbene, resveratrol, *Pterocarpus santalinus* extract, Rosemary Extract, Rosmarinic Acid, Amla extract, beta glucogallin, tetrahydrocurcumin, *Salvia Officinalis* (Sage) Leaf Extract, Ursolic Acids, Saponins, *Sesamum indicum* (Sesame) Seed Extract, Sesamin and sesamolin, moringa oil, moringa seed extract, Horse Chestnut Extract, Vitex Oil, Xymenynic Acid, ethyl ascorbic acid, Argan oil, Lemon peel extract, turmeric oil, Barley Beta Glucans, coenzyme Q10, olive oil, avocado oil and cranberry oil.

The following is a illustrative example of an composition containing ecdysterone for use as an anti-aging cream

TABLE 5

| Anti-aging Cream |
| --- |
| Active Ingredients |
| Extract containing ecdysterone<br>Coenzyme Q10, Cosmetic peptides, Tetrahydrocurcumin, *Bacillus coagulans* extracellular metabolite (Lactosporin ®) |
| Other ingredients/Excipients |
| Galanga extract, Bisabolol, Tetrahydropiperine (Cosmoperine ®)), Fragrance, Thickeners (Cellulose derivatives or Acrylates Cross Polymer), Olive Oil, Avacado Oil |

®-Registered Trademark of Sabinsa Corporation

The following is an illustrative example of an composition containing ecdysterone for use as an hair care agent.

TABLE 6

| Hair serum |
| --- |
| Active Ingredients |
| Extract containing ecdysterone<br>Amla extract, *Cocus nucifera* extract, Selenium sulphide, Vitamins |
| Excipients |
| Cationic polymers (Galsilk 700), Disodium EDTA, glycerin, Preservatives, non-ionic surfactant (Tween 20), non-ionic solubilizers and emulsifying agents (Cremophor RH 40), Bioavailability enhancers (Piperine extract or Tetrahydropiperine (Cosmoperine ®)), Fragrance, Thickeners (Cellulose derivatives or Acrylates Cross Polymer) |

TABLE 7

| Hair oil |
| --- |
| Active Ingredients |
| Extract containing ecdysterone<br>Almond oil, Amino acids (Methionine, Cysteine), Selenium Sulfide, Vitamins E, A |
| Excipients |
| Flavouring agent, Preservatives, Carrier oils, Bioavailability enhancers (Piperine extract, Tetrahydropiperine (Cosmoperine ®)), Antioxidants (rosmarinic acid) |

The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method of enhancing telomerase activity in mammalian cells, said method comprising step of bringing into contact mammalian cells with an effective concentration of ecdysterone, to bring about the effect of telomerase enhancement.

2. The method as in claim 1, wherein the mammalian cells are human cells.

* * * * *